United States Patent [19]

Raley

[11] Patent Number: 4,610,685
[45] Date of Patent: Sep. 9, 1986

[54] FIBROUS WEB WITH REINFORCED MARGINAL PORTIONS, METHOD FOR MAKING THE SAME AND ABSORBENT ARTICLE INCORPORATING THE SAME

[75] Inventor: John M. Raley, Appleton, Wis.

[73] Assignee: Kimberly-Clark Corporation, Neenah, Wis.

[21] Appl. No.: 774,111

[22] Filed: Sep. 9, 1985

[51] Int. Cl.[4] ............................................. A61F 13/16
[52] U.S. Cl. ..................................... 604/366; 604/370
[58] Field of Search ................. 604/366, 367, 365, 370

[56] References Cited

U.S. PATENT DOCUMENTS

| | | | |
|---|---|---|---|
| 2,896,626 | 7/1959 | Voigtman | 604/366 |
| 3,867,940 | 2/1975 | Mesek et al. | |
| 3,885,566 | 5/1975 | Jacob | |
| 4,055,182 | 10/1977 | Mack | |
| 4,069,822 | 1/1978 | Buell | |
| 4,147,580 | 4/1979 | Buell | 156/291 |
| 4,210,144 | 7/1980 | Sarge, III et al. | |
| 4,296,750 | 10/1981 | Woon et al. | |
| 4,337,771 | 7/1982 | Pieniak et al. | |

Primary Examiner—John D. Yasko
Attorney, Agent, or Firm—Paul Yee

[57] ABSTRACT

A fibrous web, such as a nonwoven liquid-pervious fibrous web, has reinforced marginal portions and an unreinforced medial portion, the fibers of the reinforced marginal portions being at least partially thermally fused or embedded within a cured bonding medium. A process for forming reinforced marginal portions on a fibrous web includes the steps of passing said fibrous web through a pair of nip rollers having heated marginal surface portions and at least partially thermally fusing fibers of the marginal portions, but not the medial portion, of the fibrous web. Alternatively, the method comprises applying a curable medium to the marginal portions of the fibrous web, but not to the medial portion, and curing the curable medium to embed the fibers of the marginal portions within the cured medium. The fibrous web article of the invention may suitably be employed as a liquid-pervious topsheet in an article comprising a substantially liquid-impervious backsheet, such topsheet and an absorbent body disposed therebetween.

18 Claims, 12 Drawing Figures

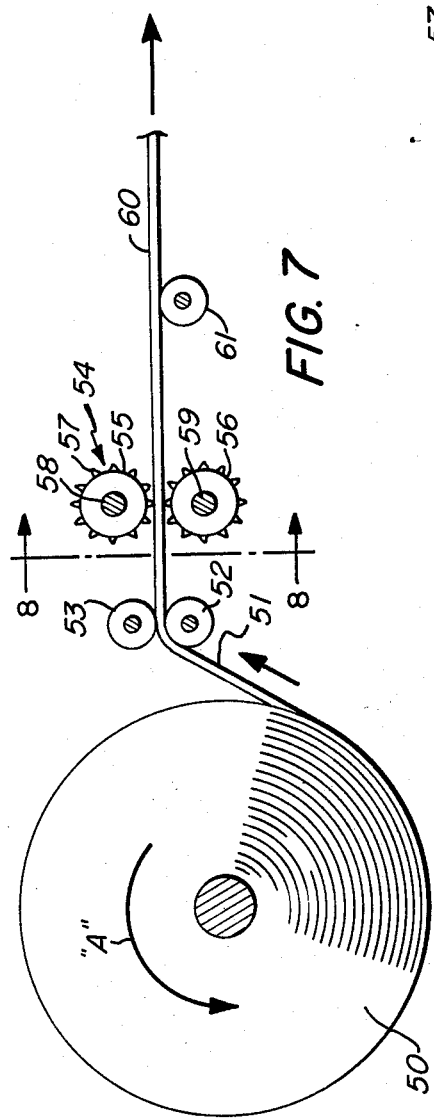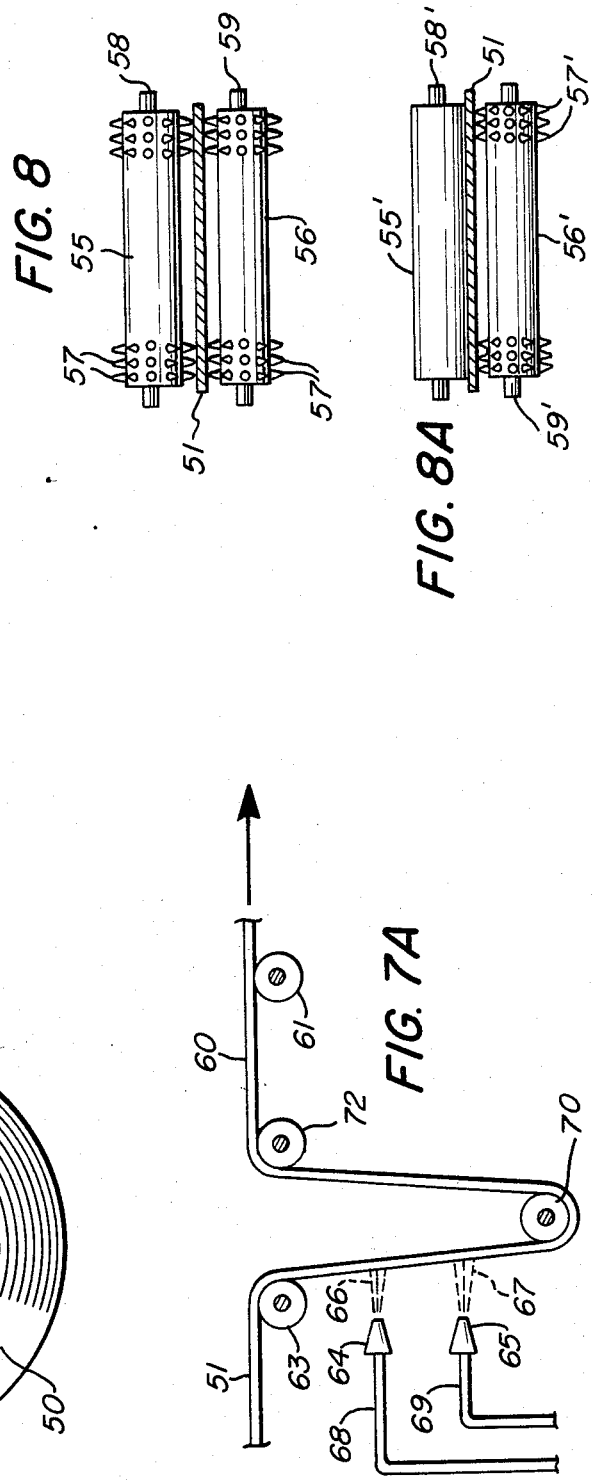

FIBROUS WEB WITH REINFORCED MARGINAL PORTIONS, METHOD FOR MAKING THE SAME AND ABSORBENT ARTICLE INCORPORATING THE SAME

BACKGROUND OF THE INVENTION

1. Field Of The Invention

This invention relates generally to fibrous webs of enhanced structural integrity and strength, to absorbent articles containing same and to a process for making such fibrous webs. More specifically, the invention relates to a fibrous web having reinforced marginal portions, to absorbent articles such as disposable diapers incorporating same, and to a process for forming reinforced marginal portions in such webs.

2. Description Of The Related Art

In the commercial manufacture of disposable diapers, incontinence garments and similar articles, it is conventional practice to utilize a web of absorbent material sandwiched between a liquid-impermeable backsheet and a liquid-permeable topsheet, the latter of which provides the skincontacting liner of the diaper or other article. Consequently, the liner should be made of a very soft material for the comfort of the wearer. Such soft materials are, however, of low tensile strength, usually comprising a nonwoven web of fibrous material. The backsheet typically is of a liquid-impervious material such as polypropylene or polyethylene sheet material.

With particular reference to disposable diapers, there is typically provided a tape fastener in upper corners of the article, attached to the topsheet and/or backsheet and featuring disposable release strips or alternatively attached at an openable end to a release area of the topsheet. As indicated above, the topsheet or liner typically is a low-tensile strength material, e.g., a spunbonded or bonded carded web liner. Accordingly, a particular problem in the usage of such disposable diaper relates to the tendency of the fixed ends of the fastener tapes to pull out from the corner or "ear" portions of the diaper, on which the fixed end of the fastener tapes are permanently affixed. Such pull-out deficiency is exacerbated by the lack of structural integrity of the topsheet or diaper liner. Although it would appear logical to increase the tensile strength of the liner in order to overcome this problem, increases in tensile strength of the liner material typically are only achieved at the sacrifice of the softness of the liner, which is unacceptable because the liner in use is placed against the skin of the wearer. Although the prior art has proposed a variety of approaches to reinforcement of various portions of disposable diaper articles, such prior approaches can be characterizable by some deficiency, such as manufacturing cost and/or complexity.

U.S. Pat. No. 3,885,566 to E. J. Jacob discloses a disposable diaper comprising a backing sheet of water-impermeable material, a facing sheet (liner) of water-permeable material, and a filling of absorbent material, with pressuresensitive tape fastening strips at the waist portion. The improvement disclosed in this patent is the provision of adhesive and/or reinforcing areas on the liner which serves as a release coat for the adhesive tape strip prior to use. The abhesive may be in the form of an applique of a silicone coating or other release liner permanently adhered to the liner surface. The patent discloses that the appliques may be made of silicone-coated release paper, silicone-coated plastic film, polyvinyl alcohol film, gelatin film, or plastic films generally which are abhesive by themselves without the need for silicone coating, such as plastic films of Teflon ®, nylon, cellophane, polyvinylchloride, polyethylene and the like. The attachment of the applique is by any means suitable, such as adhesive bonding, heat-bonding, mechanical bonding, and the like. Water-soluble appliques such as film formers suitably plasticized with water-sensitive to water-soluble plasticizers, such as corn syrup, glycerine, polyglycols and Sorbitol ® are also disclosed. The application of the applique is by coating the entire liner all over, thus insuring that the tape can rest anywhere on the facing sheet, and find an abhesive bed for itself, or for example, by applying the coating in selected patterned areas directly under the tape area. This patent thus discloses an all-over coating or a very limited tape-area coating for the disclosed applique. The all-over coating will, as discussed with reference to the disclosed materials, reduce the hand, or surface feel of the liner as well as increase the manufacturing cost of the diaper article. The tape-area application of the applique does not provide effective reinforcement of the entire ear portion of the diaper article and further, such tape-area applique is employed only on the ear portion of the diaper which provides a release surface for the "free end" of the fastener tape; the other end of the tape is permanently attached to the plastic backing sheet.

U.S. Pat. No. 4,337,771 to H. A. Pieniak, et al describes a disposable diaper having improved fit characteristics about the legs and/or waist of the wearer and having reinforced corners for enhanced securement of the diaper about the wearer. An elongated, inherently elastic ribbon member is positioned along at least one margin of the diaper, secured thereto so as to provide an elastic region at a central portion of the margin and a unitary, relatively inelastic reinforced region in a corner portion of the diaper. The ribbon member, which may be a strip of thermoplastic film, is intermittently secured to the backing and/or facing in the central portion of the diaper margin, and in such region maintains its elasticity. The end portions of the ribbon member may be rendered effectively inelastic by applying heat or other bonding energy to the desired area of attachment. The elastic means and reinforcing means is a member which is elastic in its original state and may be relaxed or have its elasticity rendered ineffective in selected portions by totally heat sealing or ultrasonically sealing those portions to the diaper backing and/or facing. Thus, the ends of the elastic members are treated to remove elasticity, so that when the diaper is relaxed the central portion of each side margin contracts and is elastic while the four corners are non-elastic but are reinforced with additional film material. The ribbon may be sealed as at two sinuous sealing lines to the backing member and the facing layer in the central portion, i.e., to the backsheet and topsheet.

U.S. Pat. No. 4,055,182 to R. J. Mack discloses a disposable diaper comprising an absorbent pad and a relatively thin sheet of flexible material covering a surface thereof. Tape fastener means are provided comprising a pressure-sensitive strip having a section secured to an outer surface of the flexible sheet in an area at least partially covering the pad. Adhesive means directly bond the sheet to the pad in a region extending from such at least partially covered area to a location spaced therefrom in a direction away from forces normally applied to the strip during placement and use of the diaper. This may for example take the form of adhesive applied to the inside of the pad assembly, such as the backing sheet, in order to directly bond the inner surface of the backing sheet to the back surface of the absorbent pad. The adhesive extends throughout a region which includes the area on which the fastener tape is affixed to the backing sheet. The adhesive area extends outwardly from the sides and end of the affixed tape strip. The patent states at column 4, lines 54–59 that the back portion of the absorbent web may preferably be saturated by adhesive throughout such region, such that the adhesive not only bonds the absorbent web to the back sheet, but also acts as a binder for the absorbent web itself. Accordingly, the adhesive is said to substantially increase the strength of the absorbent web, which also enhances the strength of the reinforcement to minimize severance of the backing sheet in the area of the fastening tape. In the disclosed diaper, the backsheet is reinforced, not the topsheet.

U.S. Pat. No. 3,867,940 to F. K. Mesek, et al. describes a multi-layer diaper including a liner, an absorbent web and a water-impervious backsheet. The backsheet is provided with adhesive tabs on its outer surface at its side portions near one end of the diaper and is reinforced with flexible structural material such as scrim, to prevent stretching and rupture of the backing sheet due to tension on the tabs generated during diapering, during the wearing of the diaper, and during its removal. The selected areas of reinforcement include the areas in the vicinity of the tab permanent attachment to the surface of the backing sheet, the front waist portion area, the marginal side portions, or the entire inner surface of the backing sheet. The scrim may be in the form of cotton gauze, polyethylene filament gauze, biaxially oriented polyethylene terephthalate films or other plastic films having a greater modulus of elasticity than the backing sheet. Again, this patent discloses to reinforce the backsheet, with no treatment being described for the topsheet or liner.

U.S. Pat. No. 4,210,144 to H. D. Sarge III, et al. discloses a disposable diaper having a backsheet, a fibrous web absorbent pad, and tape-tab fasteners having free ends which are covered on one surface with a peelable adhesive, so that the free ends can be adhesively secured to an outwardly facing region of the backsheet when the diaper is applied to a user. The disclosed improvement comprises coating on a portion of a surface of the backsheet in the mother's bond region of a material having a relatively high tensile strength and a relatively low elongation to tensile force property whereby the mother's bonds will have increased tensile strength and improved tape-tab peelability/refastenability. Preferably the coated surface is the inwardly facing surface of the backsheet. It is disclosed that a topsheet may be juxtaposed in face-to-face relation with the inwardly facing surface of the mother's bond region of the backsheet and adhesively secured together by a coating of adhesive.

U.S. Pat. No. 4,296,750 to L. S. Woon, et al. discloses a disposable diaper featuring tape closure means and an impermeable backsheet, wherein the areas of the back sheet serving as tape securement zones when the diapers are in use have uniformly adhered to that side of the film facing the diaper interior a layer of hot-melt adhesive, to impart high tear resistance to the diaper article. The hot-melt adhesive has a lower modulus of elasticity than the backsheet material and is applied in heat-softened condition to obtain strong uniform adherence to the film. The hot-melt adhesive layer may be applied across the entire extent (width) of the diaper, or alternatively in separate patches such as shown in FIGS. 4–6 of the patent which constitute the corner portions of the diaper on which the fastener tape is attached. There is no disclosed reinforcement treatment of the topsheet.

U.S. Pat. Nos. 4,069,822 and 4,147,580 to K. B. Buell describe a method of bonding a fluid-porous web to a substrate, wherein the porous web is overall or pattern coated with a hot-melt adhesive onto individual surface fibers and fiber junctions. The fluid-porous web may suitably constitute the topsheet of a disposable diaper assembly, with the topsheet being adhered by the hot-melt adhesive to a substrate which may be the backsheet and/or the absorbent web (core). Since the hot-melt adhesive is applied at only discrete localized points to the fibrous web, the adhesive is substantially invisible and the softness of the product is retained and the moisture permeability reduced only by 5% or less. FIG. 7 in the patent shows a plan view of a porous fibrous web useful as a topsheet in a diaper which is pattern coated for the hot-melt adhesive, in longitudinally extending marginal areas and narrower centrally disposed and spaced-apart longitudinal adhesive bands. The topsheet web is provided with relatively wide glue areas along its longitudinal edges, sized so as to incorporate at least a portion of the side flaps wherein elastic elements are disposed (this region is a partial cut-out to accommodate the legs of the wearer). Between the wide marginal glue areas is a plurality of narrow glue areas extending longitudinally along the web and in parallel spaced relationship. The hot-melt adhesive is applied to individual projecting surface fibers and fiber junctions of the porous web, with hot-melt adhesive globules formed on the individual projecting surface fibers and fiber junctions.

SUMMARY OF THE INVENTION

The present invention provides a fibrous web, which may be a nonwoven web, with reinforced marginal portions and an unreinforced medial portion. The reinforced marginal portions are comprised of fibers which are bonded one to the other more strongly than those of the medial portion.

In one aspect of the invention, at least the fibers of the reinforced marginal portions comprise heat-fusible fibers and are reinforced by being at least parially thermally fused one to the other. In another aspect of the invention, the fibers of the reinforced marginal portions are at least partially embedded within a cured bonding medium.

Other aspects of the invention provide that the web be of sheet form and that the reinforced marginal portions extend along the entire marginal extent thereof. Alternatively, the reinforced marginal portions may be located at corners of the sheet.

Yet another aspect of the invention provides that the web comprise fibers of a material selected from the group consisting of polyester, rayon, polypropylene and blends thereof.

One aspect of the invention provides an article comprising a substantially liquid-impervious backsheet, a liquid-pervious topsheet and an absorbent body disposed therebetween. The liquid-pervious topsheet comprises a fibrous web with reinforced marginal portions and an unreinforced medial portion, wherein the reinforced marginal portions being comprised of fibers which are bonded one to the other more strongly than the fibers of the medial portion. Generally, the article of the invention may include topsheets as described above.

In another aspect, the article of the invention may further comprise fastener means disposed at opposite corners of said article at one end thereof and within said reinforced marginal portions.

The present invention provides, in another aspect, a method for forming reinforced marginal portions on a fibrous web having an unreinforced medial portion, comprising passing at least the marginal portions of the fibrous web through a reinforcing zone or zones and reinforcing the marginal portions but not the medial portion whereby the fibers of the marginal portions are more strongly bonded to each other than the fibers of the medial portion.

In a more specific aspect of the methods of the present invention, the fibrous web is comprised at least in the marginal portions thereof of heat-fusible fibers, and the reinforcing zone comprises a thermal treatment zone, for example, heated nip rollers. The method includes the steps of passing said fibrous web through the thermal treatment zone, and heating said marginal portions in said thermal treatment zone to at least partially thermally fuse fibers in said marginal portions of said fibrous web.

In another more specific method aspect of the invention, there is provided a method wherein the reinforcement zone comprises a bonding zone, the method comprising passing said fibrous web through the bonding zone and therein applying a curable medium to the marginal portions of the web, but not to the medial portion thereof, and curing the curable medium to at least partially embed fibers of the marginal portions within the curable medium.

As used herein (and in the claims), the phrase "applying a curable medium to the marginal portions of the web" is not intended to mean or imply that the marginal portions of the fibrous web are thereby joined to any other article or surface. The recitation of the curable bonding medium is not a reference to an adhesive for attachment of the fibrous web to any other object, but is instead a reference to a curable material cured on and-/or within the fibrous web to bond fibers of the web one to the other, substantially without providing any adhesive area or adhesive coupling to any other surface or elements, e.g., to the fastener tapes or backsheet of an article including the fibrous web.

Generally, the present invention provides an inner liner for an article such as a disposable diaper, which liner has reinforced strength in its marginal portions, i.e., its transverse perimeter portions, on which the fastener tape means are affixed, usually in the corner portions or ears of the diaper.

The liner of the aforementioned type which retains its original softness in the medial areas thereof which are the regions contacting a wearer's skin.

The present invention also provides a method for forming a fibrous web suitable for use as a liner for a disposable diaper, of the aforementioned type. Other aspects and advantages of the present invention will be more fully appreciated upon a reading of the following disclosure.

BRIEF DESCRIPTION OF THE DRAWINGS

The elements and features of certain specific embodiments of the present invention will be more fully appreciated with reference to the appended drawings, wherein:

FIG. 7 is a schematic diagram of a process for forming a fibrous web according to one embodiment of the present invention;

FIG. 7A is a schematic diagram of an alternative to the process illustrated in FIG. 7 with parts omitted which are duplicative of those of FIG. 7;

FIG. 8 is an elevational view of a portion of the FIG. 7 process apparatus, taken along line 8—8 thereof; and FIG. 8A is an elevational view of an alternative thermal treatment apparatus which may be utilized in place of the apparatus shown in FIG. 8.

DETAILED DESCRIPTION OF THE PREFERRED EMBODIMENTS

It will be appreciated by those skilled in the art that all the fibers of a fibrous web are, in one sense or another, bonded to each other since otherwise a coherent web could not exist. Thus, woven or knitted fibrous webs are "bonded" together by being mechanically interweaved by the weaving, knitting or other process used to form the web. The fibers of nonwoven fibrous webs are also "bonded" to one another, for example, by being spunbonded or carded and bonded, and the resultant entanglement of the fibers may be enhanced by known means such as the inclusion of a low melting point polymer powder on the entangled fibers, which powder is fused to help hold the nonwoven fibers together. Hydraulic entanglement is also a known method to enhance the bonding of the fibers of nonwoven webs. Generally, the use of such reinforcing bonding expedients is limited or precluded when it is desired to have a soft nonwoven fabric, such as those utilized for the topsheet or liner of articles such as diapers in which softness of the material is desired. The present invention provides for reinforcing only the marginal portions of such webs by the means herein described while leaving the medial portions of the webs unreinforced so that the softness and feel thereof is not adversely affected as it inevitably would be by the reinforcement applied to the marginal portions. It will be appreciated that reference to the "unreinforced" medial portion of a web as used herein (and in the claims) merely means that the bonding technique used to form the web of desired softness for the finished article is not further reinforced as are the marginal portions. Consequently, the fibers of the reinforced marginal portions are bonded together more strongly than the fibers of the "unreinforced" medial portion.

Figure 1:
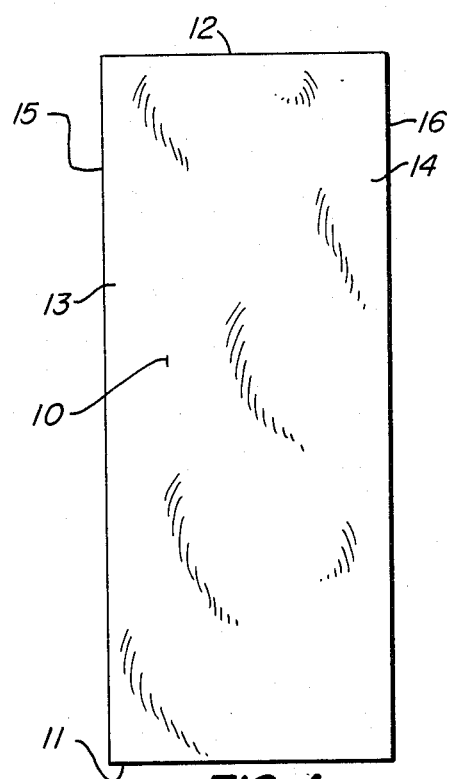
FIG. 1 is a plan view of a longitudinally extending fibrous web.

Referring now to FIG. 1, there is shown a longitudinally extending fibrous web 10 which may be formed of any suitable fibers, such as cellulosic fibers or fibers of natural, synthetic, polymeric or non-polymeric fibers, or blends thereof. A preferred fibrous web for use in the present invention is a nonwoven array of spunbonded or bonded carded fibers, which preferably are of thermoplastic or other heat-fusible material. Illustrative fibers of such type may be formed of polyester, rayon or polypropylene. The web suitably is nonwoven, but woven webs may also be used to good advantage in the broad practice of the present invention.

The web shown in FIG. 1 has a front edge 11, a back edge 12 at its longitudinal extremities, and transverse or side edges 15 and 16 defining the lateral boundaries of the transverse or marginal portions 13 and 14 of the web.

Figure 2:
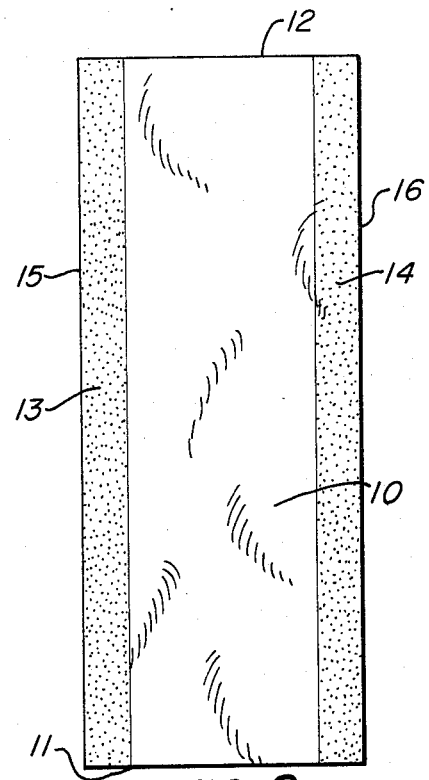
FIG. 2 is a plan view of the fibrous web of FIG. 1, having its marginal portions reinforced by at least partial thermal fusing or by coating with a cured bonding medium.

FIG. 2 is a plan view of the FIG. 1 web, which has been reinforced in its marginal portions 13 and 14 in the manner of the present invention. The reference numerals in FIG. 2 correspond to those of FIG. 1. The reinforced marginal portions 13 and 14 of the fibrous web shown in FIG. 2 are (i) at least partially thermally fused, or (ii) coated with a cured bonding medium. The first method of reinforcement associated with the web, i.e., the provision of at least partially thermally fused marginal portions, requires of course that the fibrous web comprise heat-fusible fibers, e.g., spunbonded or carded polypropylene fibers or other thermoplastic fibers. In the second method of reinforcement of marginal portions of the fibrous web, wherein the marginal portions are coated with a cured bonding medium, any suitable bonding chemicals, cements, adhesives, cured sealants, etc., may be usefully employed. Although it is satisfactory in some applications of the present invention to provide only a surface coating of the cured bonding medium on the reinforced marginal portions of the fibrous web, it is preferred in practice to maximize the reinforcement of the web by at least partially penetrating the depth of the web with the curing medium and curing the impregnated medium. By thus providing at least some degree of penetration of the cured bonding medium into the fibrous web, the bonding medium provides a reinforced matrix wherein the fibers of the web are a discontinuous phase in the continuous phase of the bonding medium. For purposes of at least partial impregnation of the web with the bonding medium, it may be desirable to utilize bonding media of a liquid type under applied pressure, to force the medium into the interstices of the fibrous web. Alternatively, the web may initially be laid or otherwise formed with the bonding medium dispersed in situ in the marginal portions of the web, with subsequent or concurrent curing of the bonding medium to produce the reinforced fibrous web according to the present invention. Naturally, it is within the purview of the invention to fully impregnate the entire depth of the web with the bonding medium so that the cured bonding medium extends from and includes opposite surfaces of the marginal portions of the web.

As can be seen from FIG. 2, since only the marginal portions 13 and 14 of the web are reinforced, the entire central region of the web is unaffected by treatment and thus retains unaffected its softness and moisture-pervious properties. In addition, the extent of reinforcement of the marginal portions may be varied to accommodate the desired end use characteristics of the fibrous web in the marginal areas.

Figure 3:
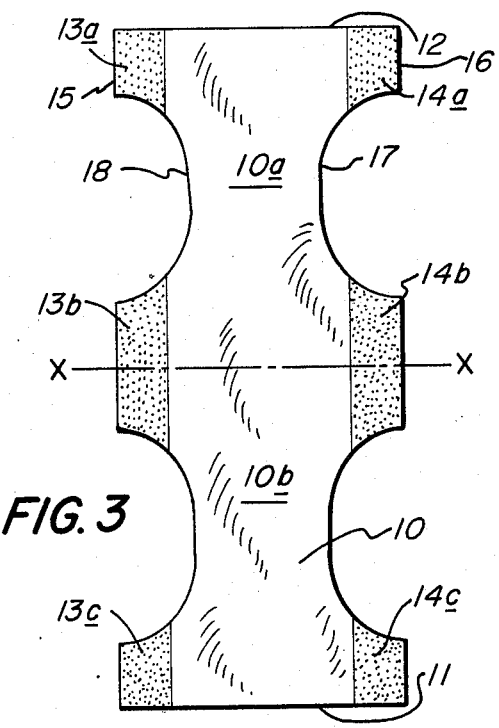
FIG. 3 is a plan view of the FIG. 2 web, which has been subjected to further processing, involving cutting marginal portions of the web.

FIG. 3 is a plan view of the longitudinally extending fibrous web of FIG. 2, wherein the same elements are labeled in accordance with the reference numerals shown in FIG. 2, but wherein the web has sections designated "a" and "b" which correspond to individual topsheet portions. The web has been cut-out at longitudinally spaced-apart intervals, in the form of the arcuate cut-outs defined by edges 17 and 18, to provide an hour-glass shape for usage in disposable diapers. These arcuate cut-outs provide accommodation to the leg areas of the wearer. As shown, the web can be incorporated into a disposable diaper construction and is severable along the transverse lines illustrated by line X—X to provide sequential discrete fibrous web articles in the disposable diaper, as is shown in FIG. 4.

Figure 4:
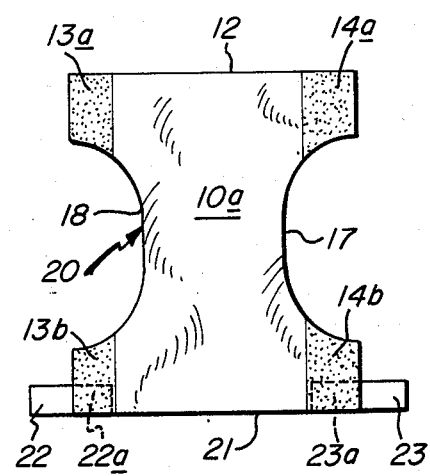
FIG. 4 is a plan view of an absorbent article formed in part from the longitudinally extending fibrous web of FIG. 3 and suitable for use as a disposable diaper.

FIG. 4 is a plan view of a disposable diaper incorporating as a topsheet or inner liner section 10a of the longitudinally extending fibrous web of FIG. 3, and a liquid-impervious backsheet, between which is sandwiched an absorbent pad, as is conventional practice. The diaper 20 features tape fasteners 22 and 23 of conventional type, which are fixedly attached at one end to the backsheet and which prior to use may be folded over to rest or otherwise adhere to the top surface of the topsheet 10a, in the corner or "ear" portions 13b and 14b, wherein the tape area of repose is indicated by dotted line outline (areas 22a and 23a). The diaper thus has a front edge 21 corresponding to the transverse line X—X in FIG. 3. In use, the tape fasteners 22 and 23 are unfolded or otherwise detached from the tape repose areas 22a, 23a and the diaper is applied to the wearer in a conventional fashion with the free ends of the tape fasteners being joined to the backsheet in the corner or ear portions 13a, 14a, respectively, to secure the diaper in place.

Figure 5:
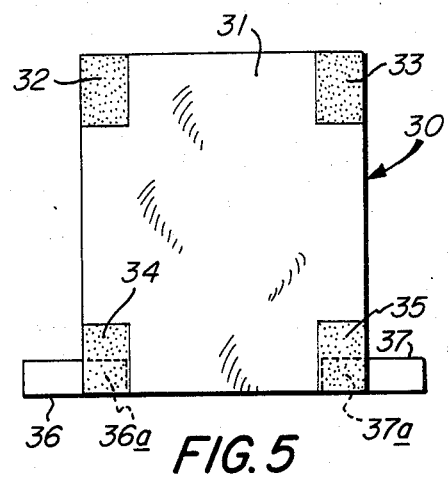
FIG. 5 is a plan view of another embodiment of an absorbent article of the present invention wherein the corner portions of the fibrous web topsheet are reinforced in the manner of the invention, at only the corners of the sheet.

FIG. 5 is a plan view of an absorbent article 30 useful as a disposable diaper and comprising a fibrous web topsheet or liner 31 whose corner regions 32, 33, 34 and 35 are reinforced in the manner of the present invention. As in the FIG. 4 embodiment, tape fastening means 36 and 37 are affixed at one end to a fluid-impervious backsheet and distal or free ends thereof are folded or detachably secured to the tape repository areas 36a, 37a on the lower corner regions 34, 35 of the topsheet 31. In use, the absorbent article is applied to the wearer in the same fashion as the FIG. 4 article, with the tape fasteners being attached at their free ends to the portions of the backsheet associated with reinforced corner regions 32 and 33. Thus, in application to a fibrous web of the type used as the topsheet in FIG. 5, it is within the purview of the present invention to reinforce marginal portions only at the corners of a fibrous web of sheet form, as opposed to reinforcement of the entire longitudinal extent of each such marginal portion, as for example is shown in the longitudinally extending fibrous web of FIG. 2.

Figure 5A:
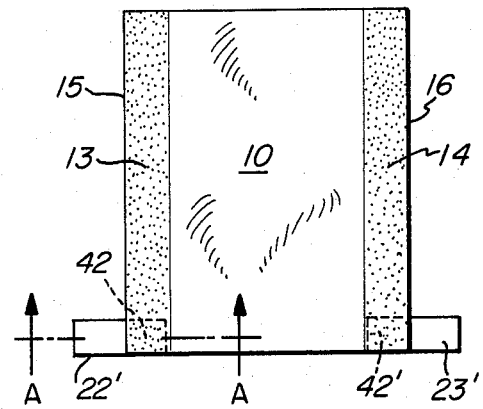
FIG. 5A is a plan view of an absorbent article formed in part from the longitudinally extending fibrous web of FIG. 2 and suitable for use as a disposable diaper.

FIG. 5A is a plan view of an absorbent article formed in part from the longitudinally extending fibrous web of FIG. 2 and suitable for use as a disposable diaper. In this article, reference numerals correspond to numbers of corresponding elements as described in FIG. 2. The absorbent article features tape fasteners 22' and 23' of conventional type, which are fixedly attached at one end to the backsheet and which prior to use may be folded over to rest on or otherwise adhere to the release layers 42 and 42' disposed on the reinforced marginal portions 13 and 14, respectively.

Figure 5B:
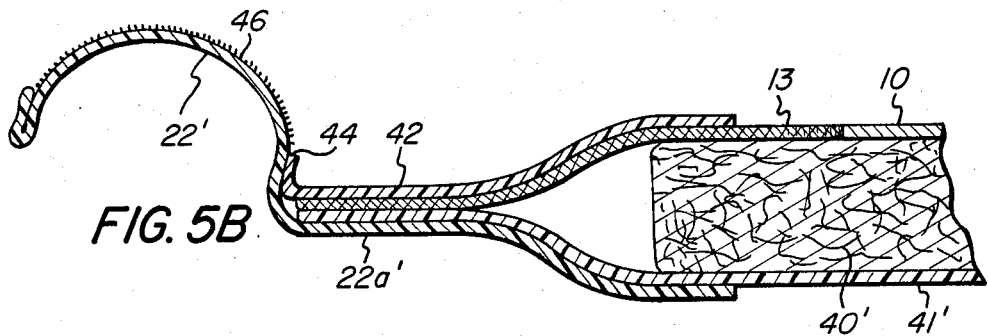
FIG. 5B is a partial end cross-sectional view taken along line A—A of FIG. 5A, showing the details of construction.

FIG. 5B shows a partial end cross-sectional view, taken along line A—A of FIG. 5A, showing the details of construction of a diaper absorbent article as shown in FIG. 5A, in particular the details of the tape fastener system therefor. The tape fastener 22' is fixedly attached to the backsheet 41' along portion 22a' of the fastener. As shown, a layer of absorbent material 40' is interposed between the backsheet 41' and the topsheet 10, the latter featuring reinforced marginal portion 13. A layer of pressure sensitive adhesive is present on surface 46 of the fastener. A layer 42 of release material, in the form of a strip of conventional release tape, is affixed to the reinforced marginal portion 13 of topsheet 10. The release layer is overlapped and affixed to fastener 22' along an overlap portion 44. During storage and prior to use, the free end of the tape, also referred to as the "mother's bond" end, is folded over and secured in place on the release layer 42. When the diaper is prepared for use, the free end of tape fastener 22' is peeled away from the release layer 42 to expose adhesive layer-coated surface 46, which allows the tape fastener to secure the diaper around the waist of the wearer.

The configuration shown in FIG. 5B wherein the release layer 42 is affixed to the reinforced marginal portion 13 of the topsheet, avoids the use of a separate disposable release strip and the dangers associated therewith, e.g., accidental ingestion by the infant of release strips not properly disposed of. The overlap portion 44 providing attachment of the release layer 42 to the tape fastener 22', allows the release layer to assist in securing the tape fastener 22' to the diaper body. The reinforced marginal portion 13 in such construction prevents the stresses induced by the release layer 42 on the topsheet from over-stressing the topsheet.

Figure 6:
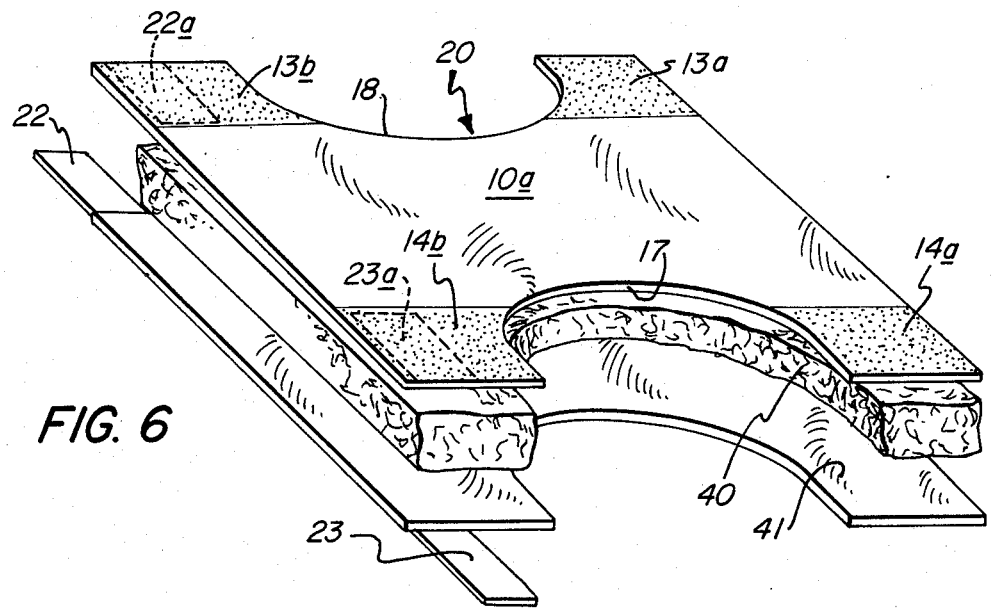
FIG. 6 is a perspective, exploded drawing of the absorbent article of FIG. 4, showing the constituent parts thereof.

FIG. 6 is an elevational exploded view of the absorbent article 20 of FIG. 4, showing the constituent parts thereof, and wherein corresponding reference numerals identify corresponding parts of the FIG. 4 drawing. As shown, the tape fasteners 22, 23 are attached at one end to the backsheet 41, which may suitably be any liquid-impervious material such as polyethylene, polypropylene or the like which may be readily fabricated in the form of a thin film, e.g., at a thickness of 1.5 mils. Between the backsheet 41 and the topsheet 10a is disposed an absorbent body 40, which may be cellulosic batting, airfelt, or other suitable absorbent pad or web material commonly used for such applications. The topsheet 10a representing the fibrous web according to the present invention with reinforced marginal ear portions 13a, 13b, 14a and 14b, may be bonded at its outer perimeter to the corresponding portions of the absorbent body 40 and/or backsheet 41. Alternatively, the topsheet 10a may be overlappingly bonded directly to the backsheet 41 at its perimetric portions, in a conventional manner.

FIG. 7 is a schematic diagram of a process for forming reinforced marginal portions on a fibrous web to yield a product fibrous web according to the present invention. At the left hand portion of the drawing, there is shown a roll 50 of fibrous web stock, which may be of a composition as described previously herein, mounted on a roll assembly in conventional manner, for rotation in the direction of Arrow A. The fibrous web 51 unwound from roll 50 passes through the nip between rolls 52 and 53, which function to tension the web, and passes to a thermal treatment zone comprising in the illustrated embodiment, a pair of nip rollers 55 and 56 which are mounted respectively on shafts 58 and 59, which in turn are coupled to means for rotating the nip rollers, such as an electric motor or other drive means (not shown). The nip rollers 55 and 56 of the nip roller assembly 54 each have marginal arrays of surface protrusions 57 which matingly face one another during rotation of the respective rollers, as best seen in FIG. 8. The contoured surface portions at the margins of the respective nip rollers 55 and 56 are suitably heated when the fibrous web is formed of a material comprising thermoplastic or heat-fusible fibers, to at least partially thermally fuse transverse marginal portions of the fibrous web 51 passed therethrough.

FIG. 8A illustrates alternative thermal treatment apparatus which may be used in place of the nip roller assembly 54 as shown in FIG. 8. The alternative apparatus employs the dissimilar nip rollers 55' and 56', roller 56' having a marginal array of surface protrusions 57', while roller 55' has a substantially smooth outer cylindrical surface. The respective rollers 55' and 56' are mounted for rotation on shafts 58' and 59', respectively, which are coupled to suitable means for rotation thereof (not shown). The fibrous web 51 is nipped between the protrusions 57' of roller 56' and the smooth outer cylindrical surface of roller 55'. Roller 56' is suitably heated, to at least partially thermally fuse transverse marginal portions of the fibrous web passed through the nip defined by these rollers.

After passage through the nip roller assembly 54, FIG. 7 the product web having reinforced marginal portions which are at least partially thermally fused is passed as product web 60 over the guide roll 61 to end use fabrication and processing steps. The longitudinally extending product web 60 corresponds to the partial plan view of the fibrous web shown in FIG. 2. It will be appreciated that the reinforced marginal portions 13 and 14 of FIG. 2 may be considered areas containing a random or repeating pattern of fused areas separated by unfused areas, such as a diamond or checkerboard pattern, or they may comprise areas which are entirely fused, such as by thermally fusing the fibrous web with smooth, heat-applying rollers.

Alternatively, the FIG. 7 process system may be adapted to provide reinforced marginal portions of the fibrous web which are coated with a cured bonding medium as illustrated in FIG. 7A. In this alternative embodiment, the thermal treatment zone provided by the nip roller assembly 54 of FIG. 7 may be combined with or replaced by a bonding zone provided, in the illustrated embodiment, by nozzles 64 and 65 and the conduits joined thereto as more fully described below. Fibrous web 51 of FIG. 7A is supplied from a roll (not shown) such as roll 50 of FIG. 7 and is directed by means of guide rolls 63 and 70 past a bonding zone comprising bonding medium application nozzle 64, which is joined by feed conduit 68 to a source of uncured bonding medium (not shown). The bonding medium is applied in a spray 66 to the presented surface of the fibrous web, which subsequently passes to the air-drying zone defined by hot air discharge nozzle 65, which is joined by conduit 69 to a source of compressed air at elevated temperature (not shown). The nozzle 65 discharges a stream 67 of air at elevated temperature onto the web portions (margins) to which the bonding medium previously was applied by bonding medium nozzle 64. It will be appreciated that the bonding medium being applied to the marginal portions of the fibrous web will be suitably applied by laterally or transversely spaced-apart nozzles of the type illustrated as nozzle 64 and the drying zone will suitably comprise to laterally spaced-apart nozzles of the type shown as element 65. The elevated temperature gas stream flows against the web and produces a thermal cure of the previously applied bonding medium, with the product web 60 having reinforced marginal portions coated with the cured bonding medium being directed by guide rolls 70, 72 and 61 to downstream fabrication and/or further processing steps. Thus, the product fibrous web 60 having reinforced marginal portions may travel downstream for lamination with the backsheet and absorbent body 40 shown in FIG. 6, to produce disposable diaper absorbent articles.

Although in the alternative embodiment shown in FIG. 7A, the bonding medium is cured by elevated temperature conditions mediated by the flow of air against the web downstream of the bonding medium application apparatus, it will be appreciated that bonding media curing by other than temperature gradient may be usefully employed in the broad practice of the present invention. For example, the apparatus of the alternative type shown in FIG. 7A could be employed wherein a first set of nozzles 64 applies a first component of a two-component bonding medium, with the second component being applied by nozzles 65.

It is within the purview of the invention to reinforce longitudinally extending portions of a web, which portions are located not at the web margins but interiorly thereof in medial or central longitudinally extending portions of the web, provided that the web is subsequently longitudinally cut into strips or narrower webs so that, after such cutting, only marginal portions of the cut strips or narrower webs are reinforced. In this manner, the resulting (from the cutting) medial portions are left unreinforced and thus retain their original softness. Thus, reference herein (including the claims) to "marginal portions" is defined to include portions which become marginal portions only after cutting, which may take place after longitudinally extending strips of the web are reinforced.

Further, although illustrated embodiments of the present invention have been shown and described hereinabove, it will be appreciated that other modifications, variants and modifications are possible, and all apparent modifications, variants and embodiments are to be regarded as being within the spirit and scope of the present invention.

What is claimed is:

1. A fibrous web with reinforced marginal portions and an unreinforced medial portion, wherein the reinforced marginal portions are comprised of fibers which are bonded one to the other more strongly than those of the medial portion, and wherein said stronger bonding provides said reinforcement substantially without coupling said fibrous web to another object.

2. A fibrous web according to claim 1, wherein at least a portion of the fibers of the reinforced marginal portions comprise heat-fusible fibers and are reinforced by being at least partially thermally fused one to the other.

3. A fibrous web according to claim 1 wherein the fibers of the reinforced marginal portions are at least partially embedded within a cured bonding medium.

4. A fibrous web according to claim 1 comprising a nonwoven web.

5. A fibrous web according to any one of claim 1, claim 2, claim 3 or claim 4, wherein said web is of sheet form and said reinforced marginal portions extend along the entire marginal extent thereof.

6. A fibrous web according to any one of claim 1, claim 2, claim 3 or claim 4, wherein said reinforced marginal portions are located at corners of said sheet.

7. A fibrous web according to claim 1, wherein said web comprises fibers of a material selected from the group consisting of polyester, rayon, polypropylene and blends thereof.

8. An article comprising a substantially liquid-impervious backsheet, a liquid-pervious topsheet and an absorbent body disposed therebetween, the improvement comprising that said liquid-pervious topsheet comprises a fibrous web with reinforced marginal portions and an unreinforced medial portion, wherein the reinforced marginal portions are comprised of fibers which are bonded one to the other more strongly than those of the medial portion, and wherein said stronger bonding provides said reinforcement substantially without coupling said fibrous web to another object.

9. An article according to claim 8, wherein said fibrous web comprises heat-fusible fibers at least in the marginal portions thereof and wherein the fibers in said reinforced marginal portions are at least partially thermally fused one to the other.

10. An article according to claim 8, wherein the fibers of said reinforced marginal portions are at least partially embedded in a cured bonding medium.

11. An article according to claim 8, wherein said fibrous web is of sheet form, and said reinforced marginal portions extend along the entire marginal extent thereof.

12. An article according to claim 8, wherein said fibrous web is of sheet form and said reinforced marginal portions are located at corners of said web.

13. An article according to claim 8, further comprising fastener means disposed at opposite corners of said article at one end thereof and within said reinforced marginal portions.

14. A method for forming reinforced marginal portions on a fibrous web having an unreinforced medial portion, comprising passing at least the marginal portions of the fibrous web through a reinforcing zone or zones and reinforcing the marginal portions but not the medial portion, thereby forming reinforced marginal portions wherein the fibers are bonded one to the other more strongly than those of the medial portion, and wherein said stronger bonding provides said reinforcement substantially without coupling said fibrous web to another object.

15. A method according to claim 14, wherein the fibrous web is comprised at least in the marginal portions thereof of heat-fusible fibers and the reinforcing zone comprises a thermal treatment zone, the method comprising passing said fibrous web through the thermal treatment zone, heating said marginal portions in said thermal treatment zone to at least parially thermally fuse fibers in said marginal portions of said fibrous web.

16. A method according to claim 15, wherein the thermal treatment zone comprises nip rollers having heated surface portions which heat said marginal portions of said web under pressure to thermally fuse fibers in said marginal portions.

17. A method according to claim 16, wherein said heated surface portions of said nip rollers have disposed thereon arrays of surface protrusions which emboss the marginal portions of said fibrous web.

18. A method according to claim 14, wherein the reinforcement zone comprises a bonding zone, the method comprising passing said fibrous web through the bonding zone and therein applying a curable medium to the marginal portions of the web, but not to the medial portion thereof, and curing the curable medium to embed fibers of the marginal portions within the curable medium.

* * * * *